United States Patent [19]

Dolling et al.

[11] 4,149,012

[45] Apr. 10, 1979

[54] SYNTHESIS OF RACEMIC 3-FLUORO-ALANINE AND ITS SALTS

[75] Inventors: Ulf-H. Dolling; Edward J. J. Grabowski, both of Westfield; Erwin F. Schoenewaldt, Watchung; Meyer Sletzinger, North Plainfield, all of N.J.

[73] Assignee: Merck & Co., Inc., Rahway, N.J.

[21] Appl. No.: 840,335

[22] Filed: Oct. 7, 1977

Related U.S. Application Data

[63] Continuation-in-part of Ser. No. 664,329, Mar. 5, 1976, abandoned, which is a continuation of Ser. No. 522,184, Nov. 8, 1974, abandoned.

[51] Int. Cl.² ............................................. C07C 99/00
[52] U.S. Cl. .................................... 562/574; 562/560; 562/561
[58] Field of Search ...................... 260/534 L; 562/574

[56] References Cited

U.S. PATENT DOCUMENTS 2,610,212  9/1952  Floyd ................................ 260/534 R
2,839,547  6/1958  Borther ............................ 260/534 L

FOREIGN PATENT DOCUMENTS 38-6884  5/1963  Japan ................................... 260/534 R

OTHER PUBLICATIONS

Greenstein, "Chemistry of the Amino Acids," vol. 3, (Wiley & Sons, Inc., N.Y., 1961), p. 1829.
Borch, J. Am. Chem. Soc., 93, pp. 2897–2904 (1971).

*Primary Examiner*—James O. Thomas, Jr.
*Assistant Examiner*—Michael Shippen
*Attorney, Agent, or Firm*—Hesna J. Pfeiffer; Julian S. Levitt

[57] ABSTRACT

The racemate of 3-fluoro-alanine, and salts thereof, are prepared by reductive amination of 3-fluoro-pyruvic acid, its hydrate, or salts thereof, via the intermediate 2-imino-3-fluoro propionic acid salt, using alkali metal borohydrides as reducing agents. The racemates thus obtained are valuable in the production of 3-fluoro-D-alanine and its pharmacologically acceptable salts, and derivatives thereof, which are potent antibacterial agents.

3 Claims, No Drawings

SYNTHESIS OF RACEMIC 3-FLUORO-ALANINE AND ITS SALTS

RELATIONSHIP TO PRIOR APPLICATIONS

This is a continuation-in-part of U.S. Ser. No. 664,329, filed Mar. 5, 1976, now abandoned, which was in turn a continuation of U.S. Ser. No. 522,184, filed Nov. 8, 1974, now abandoned.

SUMMARY OF THE INVENTION

This invention is concerned generally with the production of the racemate of 3-fluoro-alanine which is valuable as an intermediate for preparing 3-fluoro-D-alanine, its salts and esters, potent antibacterial agents effective in inhibiting the growth of pathogenic bacteria of both the gram positive and gram negative type. More particularly, it relates to the process for converting 3-fluoro-pyruvic acid, its hydrate or salt thereof (e.g. lithium fluoropyruvate hydrate), to racemic 3-fluoro-alanine by a reductive amination procedure in which a salt of 3-fluoro-pyruvic acid, or hydrate thereof, is subjected to reductive amination with an alkali metal borohydride, thereby forming directly a salt of racemic 3-fluoro-alanine; it also relates to the novel lithium fluoro-pyruvate hydrate, intermediate in this reductive amination procedure.

This reductive amination reaction is conveniently conducted by first equilibrating a salt of fluoropyruvic acid hydrate (e.g. lithium 2,2-dihydroxy-3-fluoro-propionate) in aqueous ammoniacal solution with formation of the corresponding salt of 2-amino-2-hydroxy-3-fluoro-propionic acid (e.g. lithium, sodium or ammonium 2-amino-2-hydroxy-3-fluoro-propionate) and the salt of 2,2-diamino-3-fluoro-propionate; the equilibrium ratio of 2,2-diamino-3-fluoro-propionate to 2-amino-2-hydroxy-3-fluoro-propionate thus formed is a function of ammonia concentration and, in concentrated aqueous ammonia (13 N), the ratio is approximately 95 to 5. Although not ordinarily preferred, lower aqueous ammonia concentrations may be used; for example with 6.5 N aqueous ammonium hydroxide, the equilibrium ratio is approximately 90 to 10. Upon reduction, this mixture would necessarily result in a reduced yield of 3-fluoro-DL-alanine and an increased amount of 3-fluoro-lactate by-product. The equilibration at 37° C. is a pseudo-first-order reaction with a half-life of 15 minutes; equilibration at 37° C. for 90 minutes provides six half-lives, and an effective ratio of 2,2-diamino-3-fluoropropionate to 2-amino-2-hydroxy-3-fluoro-propionate of 95 to 5. Although the 2,2-diamino-3-fluoropropionate salt is not isolated from the ammonia solution, its presence, in a purity of 95%, is readily demonstrated by NMR (nuclear magnetic resonance) measurement.

The 2,2-diamino-3-fluoropropionate is itself in equilibrium, by loss of ammonia, with a minor proportion of the "2-imine" (the 2-imino-3-fluoro-propionate); and the 2-amino-2-hydroxy-3-fluoro-propionate is likewise in equilibrium, by loss of ammonia, with a minor proportion of "carbonyl" or "2-ketone" (i.e. the fluoro-pyruvate or 2-keto-3-fluoro-propionate). In the alkali metal borohydride reduction operation, it is the "2-imine" and "carbonyl" (not the ammonia solvate forms) which undergo reduction; as "imine" and "carbonyl" are reduced, the 2,2-diamino and 2-amino-2-hydroxy species are rapidly converted to the imine and carbonyl, respectively. The discovery, that the "2-imine" can be efficiently reduced to the "2-amine" using an alkali metal borohydride, and particularly that this reduction can be conducted in aqueous solution and even in the presence of concentrated aqueous ammonia, was indeed surprising.

Moreover, the desired reduction of the imine group to form 3-fluoro-alanine proceeds more slowly than does the reduction of carbonyl to form 3-fluoro-lactate. Accordingly, concentrated aqueous ammonia is ordinarily employed in the initial equilibration reaction to achieve the highest ratio of 2,2-diamino-3-fluoro-pyruvate to 2-amino-2-hydroxy-3-fluoro-pyruvate (i.e. 95:5), and the reduction reaction is preferably conducted as rapidly as possible, relative to the rate of reverse equilibration* of the 2,2-diamino-3-fluoropyruvate to 2-amino-2-hydroxy-fluoropyruvate. This rapid reduction is conveniently accomplished by using a large (up to five-fold) excess of alkali metal borohydride reducing agent.

*This reversal of 2,2-diamino species to 2-amino-2-hydroxy species necessarily occurs when the carbonyl group, due to its more rapid reduction, is preferentially removed from the reaction solution.

It is preferred, however, to employ only a small (i.e. 50%) excess of borohydride reducing agent; under such circumstances, the rate of reduction of imine would be reduced, the reverse equilibration could occur to a very considerable degree, and formation of the unwanted by-product 3-fluoro-lactate would be substantially increased. It is a preferred embodiment of this invention, that this unwanted/reverse equilibration can be minimized while employing only a 50% excess of borohydride reducing agent. This is achieved by adding the borohydride reducing agent to the equilibrium solution, and then rapidly evaporating excess ammonia from the solution; at the resulting reduced pH (corresponding to substantial removal of excess ammonia) the borohydride reduction is extremely rapid. It is a feature of the invention that the evaporative removal of the ammonia be accomplished sufficiently rapidly so that the thereby greatly accelerated borohydride reduction effectively reduces all imine to amine before there can occur any substantial reverse equilibration of 2,2-diamino-3-fluoropyruvate to 2-amino-2-hydroxy-3-fluoropyruvate (which would otherwise result from this reduced ammonia concentration). While with flash evaporating equipment, the parameters above indicated can be readily achieved at room temperature or above, it has been found convenient in batch operations to "freeze" the equilibrium at 95 parts 2,2-diamino-3-fluoropyruvate to 5 parts 2-amino-2-hydroxy-3-fluoropyruvate in concentrated aqueous ammonia by cooling the mixture to 10° C., at which temperature the equilibration half-life (which is 15 min. at 37° C.) is increased to approximately five hours; the borohyride reducing agent is then added to the cold solution. Although, in this concentrated aqueous ammonia solution at 10° C., the rate of borohydride reduction of imine is relatively slow, the rate of reduction (using this low temperature and small excess borohydride reducing agent) is greatly increased (so that the reduction of imine to amine occurs in a period of only ten minutes) by evaporative removal of excess ammonia; such evaporation is conducted under reduced pressure while maintaining the temperature at about 10° C.

Thus, the preferred procedure in accordance with the present invention, which effectively combines the above-noted features, involves (a) equilibration of a fluoropyruvate salt, preferably an alkali metal or alkaline earth metal salt, or an ammonium salt, e.g. ammonium fluoropyruvate, sodium fluoropyruvate, lithium fluoropyruvate, hydrate, and the like, preferably at about 37° C., in concentrated aqueous ammonia at which temperature there is obtained a 95:5 ratio 2,2-diamino-3-fluoropyruvate:2-amino-2-hydroxy-3-fluoropyruvate in about 90 minutes; it is particularly advantageous to employ the novel lithium fluoropyruvate hydrate, since the latter, in contrast to other alkali metal fluoropyruvates, is relatively insoluble in water and is readily prepared, in accordance with the presently invented process, in pure form and high yield; (b) addition of alkali metal borohydride, such as sodium borohydride, lithium borohydride, and the like, after cooling to 10° C., if desired, to freeze the equilibrium; (c) evaporative removal of excess ammonia sufficiently rapidly so that accelerated borohydride reduction effectively reduces imine to amine before substantial reverse equilibration occurs to form 2-amino-2-hydroxy-3-fluoropyruvate; at the preferred 10° C. temperature, equilibration half-life is increased to five hours, whereas complete reduction of imine to amine occurs in only about 10 minutes. The reduction reaction may be conducted, if desired, at room temperature or above without evaporating excess ammonia from the concentrated aqueous ammonia solution, but this procedure results in poorer yields.

Following the reductive amination reaction, the reaction mixture is evaporated in vacuo until water distills, thereby substantially removing all ammonia present, since residual ammonium ions transfer in the ion-exchange column purification. The substantially ammonia-free reaction solution is then acidified with an aqueous mineral acid, such as aqueous hydrochloric acid, thereby cleaving the boron complex of 3-fluoro-alanine formed during the reductive amination reaction. The acidified reaction mixture, which is conveniently freed of colored impurities which may be present by treatment with activated charcoal, is then passed through a column containing an acid pre-washed, strongly-acidic, cation-exchange resin such as Dowex 50W-X4 and Dowex 50W-X8*, thereby separating the desired 3-fluoro-alanine from the by-product fluoro-lactic acid and metallic cations. The ion exchange column containing the adsorbed 3-fluoro-alanine is washed with de-ionized water until the eluate is no longer acidic, and the column is then eluted with dilute aqueous ammonium hydroxide solution whereupon ammonium ion replaces the 3-fluoro-alanine on the resin column. The eluate is then evaporated in vacuo, thereby removing any ammonia present in the eluate; the colored solution is decolorized and evaporated in vacuo. The residual material is crystallized from aqueous alkanol, preferably aqueous isopropanol, to give the 3-fluoro-alanine in substantially pure form.

*Dowex 50W-X4 is a strongly acidic, cation-exchange resin consisting of a sulfonated styrene-divinylbenzene copolymer containing 4% divinylbenzene, having a mesh size 20–50 mesh based on the U.S. standard screen; Dowex 50W-X8 is similar to Dowex 50W-X4 except that it contains 8% divinylbenzene in the sulfonated styrene-divinylbenzene copolymer.

The following examples illustrate methods of carrying out the present invention, but it is to be understood that these examples are given for purposes of illustration and not of limitation.

EXAMPLE 1

A mixture of 400 ml. of ethyl ether and 240 ml. of 5 N aqueous hydrochloric acid is cooled to a temperature of about −15° to −20° C. To this mixture is added, with good stirring and under a nitrogen atmosphere, about 138 grams of lump-free ethyl ethoxalyl-fluoroacetate sodium salt at a steady rate such that the temperature remains between about −15° C. and −20° C. When addition is complete, the mixture is warmed to room temperature, diluted with 240 ml. of water, and the aqueous-ethereal mixture is heated at atmospheric pressure and the ether is distilled until the temperature of the aqueous solution reaches about 102°–105° C. The resulting aqueous solution is then heated under reflux for a period of about 4 hours. The reaction solution is cooled to room temperature, stirred with about 6 grams of activated charcoal (Darco G-60), filtered through acid-prewashed diatomaceous silica (Supercel), and the insoluble material on the filter washed with a minimum of water. The filtered solution is cooled to about 0°–5° C.; neutralized with pH control, by addition of solid lithium hydroxide hydrate (about 47 grams of LiOH.H$_2$O required) to a final pH of 6.0 to 6.5; and the resulting neutralized slurry is allowed to stand at about 0° C. for a period of approximately 15 hours. The precipitated material is recovered by filtration, washed with a minimum of cold water, then with two 200 ml.-portions of methanol, and then with 200 ml.-portions of acetone. The resulting material is air-dried to give about 56 grams of lithium fluoropyruvate hydrate.

EXAMPLE 2

About 26 grams of lithium fluoropyruvate hydrate is added, with good agitation and at room temperature, to about 300 ml. of concentrated (25–28%) aqueous ammonium hydroxide. The resulting suspension is heated to about 37° C. (whereupon substantially all of the solid material dissolves), and the solution is maintained at that temperature for a period of about 1.5 hours. The resulting dark solution, which contains about 95 parts of 2,2-diamino-3-fluoro-propionate to about 5 parts of 2-amino-2-hydroxy-3-fluoro-propionate, is cooled to about 25° C., placed under a nitrogen atmosphere, and about 7.6 grams (a four-fold excess) of sodium borohydride is added. The reaction, which occurs, is exothermic, and the temperature rises to about 30° C. The reaction mixture is then heated to about 37° C. and maintained at that temperature for a period of about 3 hours, at the end of which time the reductive amination reaction mixture is substantially complete.

The reaction mixture is distilled under reduced pressure until about 50 ml. of water has been evaporated from the mixture, thereby insuring substantially complete removal of ammonia, and the residual solution is cooled to about 0° C. To this solution is added, with stirring and cooling to maintain the temperature at about 0°–5° C., about 165 ml. of 2.5 N aqueous hydrochloric acid solution. The acidified reaction solution is warmed to room temperature, stirred with 1.3 grams of activated charcoal (Darco G-60) for about 15 minutes, and filtered.

The filtered solution is diluted with an equal volume of water, and slowly passed through a column containing 800 ml. of an acid pre-washed, strongly acidic, cation-exchange resin (Dowex 50W-X4). The column is washed with de-ionized water until the eluate is no longer acidic (about 4 liters water required), and the column is then eluted with 0.5 N aqueous ammonium hydroxide solution. The 3-fluoro-DL-alanine comes off immediately before the ammonia breakthrough; the elution is monitored with ninhydrin reagent spray on a test spot on a thin layer chromatogram plate. The ammonia "front" can be detected as a warm band proceeding down the column. The end of the 3-fluoro-DL-alanine elution customarily trails into the ammonia breakthrough. The eluate (volume approximately 1200 ml.) is evaporated in vacuo, at a temperature not exceeding 25° C., to form a slurry of about 75 ml volume, and the precipitated material is redissolved by heating the slurry to about 60° C. To the resulting slurry (at 60° C.) is added about 50 ml of preheated isopropanol (also at 60° C.), whereupon the mixture becomes cloudy, and the aqueous isopropanol solution is allowed to cool to room temperature. The slurry thus obtained is cooled to about 0° C., allowed to stand at this temperature for about one to two hours, and the resulting crystalline slurry is filtered. The crystalline material is filtered, washed with two 20 ml portions of cold 90% isopropanol, and vacuum dried at 40° C. to give about 11 grams of 3-fluoro-DL-alanine.

EXAMPLE 3

To about 150 ml of concentrated aqueous ammonium hydroxide is added, with good agitation and at room temperature, 18.35 grams of lithium fluoro-pyruvate. The resulting suspension is heated to about 35°–37° C. (whereupon substantially all of the solid material dissolves), and the solution is maintained at that temperature for a period of about 1.5 hours; the resulting solution, which contains about 95 parts of 2,2-diamino-3-fluoropropionate to 5 parts of 2-amino-2-hydroxy-3-fluoropyruvate and which may contain dark colored impurities, is cooled to about 10° C., and to this cold solution is added about 8.5 grams of solid lithium chloride and 1.785 grams of sodium borohydride. The resulting solution is placed under vacuum with stirring and vigorous subsurface nitrogen flow to remove dissolved ammonia. The temperature of the solution is maintained at 10°–13° C. for a period of about 1 hour, then gradually raised to about 25° C. over a 1 hour period, and held at 28°–33° C. for a period of about 1.5 hours. The reaction solution is evaporated in vacuo at 35° C. until water distills and the solution is essentially free of ammonia, and the resulting solution is then acidified with about 80 ml of 2.5 N aqueous hydrochloric acid solution. The acidified reaction solution is stirred with about 2.5 grams of activated charcoal (Darco KB) for about 15 minutes and filtered.

The filtered solution is slowly passed through a column containing 850 ml of acid pre-washed, strongly acidic, cation-exchange resin (Dowex 50W-X4). The column is washed with de-ionized water until the eluate is no longer acidic (about 4 liters water required), and the column is then eluted with 0.5 N aqueous ammonium hydroxide solution. The ninhydrin-positive fractions are combined, and evaporated in vacuo at a temperature not exceeding 30° C., to give about 400 ml of an ammonium-free solution. This solution is stirred at room temperature with 2.5 grams of activated charcoal (Darco KB); the charcoal is removed by filtration, the filtered solution is again stirred with an additional 1.5 grams of activated charcoal, and the slurry is again filtered. The filtered solution is evaporated to dryness in vacuo at a temperature not exceeding 30° C. to give about 7.3 grams of crude material.

This material is dissolved in 33 ml of water at a temperature of about 60° C.; about 27 ml of isopropanol (preheated to 60° C.) is added; the aqueous isopropanol solution is seeded with crystals of 3-fluoro-DL-alanine; and the resulting mixture is cooled slowly first to room temperature and then to about 0° C. The crystalline slurry is allowed to stand at 0° C. for about 1–2 hours, the slurry is filtered, and the crystalline material on the filter is washed with two 5 ml-portions of 90% aqueous isopropanol, then with two 5 ml-portions of isopropanol, and finally with hexane. The washed material is dried in vacuo at a temperature of 50°–60° C. to give about 5.6 grams of 3-fluoro-DL-alanine.

Various changes and modifications may be made in carrying out the present invention without departing from the spirit and scope thereof. Insofar as these changes and modifications are within the purview of the annexed claims, they are to be considered as part of this invention.

What is claimed is:

1. The process which comprises reacting an alkali metal or alkaline earth metal salt of 3-fluoropyruvic acid or hydrate thereof, with aqueous ammonium hydroxide until substantially converted to a salt of 2,2-diamino-3-fluoropropionic acid, and reacting the latter with an alkali metal borohydride to produce a salt of 3-fluoro-DL-alanine.

2. The process as defined in claim 1, which comprises reacting a salt of 3-fluoropyruvic acid hydrate with concentrated aqueous ammonium hydroxide for a time sufficient to convert substantially all of the 3-fluoropyruvic acid to 2,2-diamino-3-fluoropropionate salt, cooling the resulting solution to a temperature of about 10° C. thereby substantially stabilizing the 2,2-diamino-3-fluoropropionic acid component of said solution against the reverse reaction to form 2-amino-2-hydroxy-3-fluoropyruvic acid compound, adding alkali metal borohydride to this cold aqueous ammoniacial solution and subjecting the resulting solution to distillation under reduced pressure while maintaining the temperature at about 10° C. until substantially all of the excess ammonia is evaporated from said solution, and maintaining the resulting solution at 10° C. for a period of about 10 min. to form a salt of 3-fluoro-DL-alanine.

3. The process, as defined in claim 1, which comprises reacting lithium 3-fluoropyruvate hydrate with concentrated aqueous ammonium hydroxide at a temperature at about 37° C. for a period of about 90 minutes thereby forming an equilibrium solution containing about 95 parts of 2,2-diamino-3-fluoro-propionate salt and about 5 parts of 2-amino-2-hydroxy-3-fluoropropionate salt; cooling the resulting aqueous ammoniacal solution to a temperature of about 10° C. thereby substantially stabilizing the 2,2-diamino-3-fluoro-propionate component against the reverse reaction to form 2-amino-2-hydroxy-3-fluoropyruvate; adding to this cold aqueous ammoniacal solution approximately 1.5 equivalents of sodium borohydride; subjecting the resulting solution to distillation under reduced pressure at 10° C. until substantially all of the excess ammonia is evaporated; and maintaining the resulting solution at 10° C. for a period of about 10 minutes, to produce a salt of 3-fluoro-DL-alanine.

* * * * *